United States Patent
Usui et al.

(10) Patent No.: US 8,450,058 B2
(45) Date of Patent: May 28, 2013

(54) METHOD OF DETECTING TARGET SUBSTANCE

(75) Inventors: Mitsugu Usui, Kawasaki (JP); Chikako Hakii, Kawasaki (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 440 days.

(21) Appl. No.: 12/733,164

(22) PCT Filed: Aug. 11, 2008

(86) PCT No.: PCT/JP2008/064422
§ 371 (c)(1),
(2), (4) Date: Feb. 16, 2010

(87) PCT Pub. No.: WO2009/022682
PCT Pub. Date: Feb. 19, 2009

(65) Prior Publication Data
US 2010/0151592 A1   Jun. 17, 2010

(30) Foreign Application Priority Data

Aug. 14, 2007   (JP) ................................. 2007-211521

(51) Int. Cl.
*C12Q 1/68* (2006.01)
*C07H 21/00* (2006.01)
*C07H 21/02* (2006.01)
*C07H 21/04* (2006.01)

(52) U.S. Cl.
USPC .......... 435/6.1; 536/22.1; 536/23.1; 536/24.3

(58) Field of Classification Search
USPC .................. 435/6.1; 536/23.1, 24.3
See application file for complete search history.

(56) References Cited

U.S. PATENT DOCUMENTS

| | | | | |
|---|---|---|---|---|
| 5,424,413 A | * | 6/1995 | Hogan et al. | 536/24.31 |
| 5,437,977 A | * | 8/1995 | Segev | 435/6.12 |
| 5,635,352 A | * | 6/1997 | Urdea et al. | 435/6.18 |
| 2005/0130139 A1 | * | 6/2005 | Usui et al. | 435/6 |
| 2006/0035235 A1 | * | 2/2006 | Usui et al. | 435/6 |
| 2006/0210983 A1 | | 9/2006 | Usui et al. | |
| 2008/0160624 A1 | | 7/2008 | Fujikawa et al. | |
| 2008/0199968 A1 | | 8/2008 | Ichihara et al. | |
| 2010/0160179 A1 | | 6/2010 | Usui et al. | |

FOREIGN PATENT DOCUMENTS

| | | |
|---|---|---|
| CA | 2 599 537 | 9/2006 |
| EP | 1 595 953 | 11/2005 |
| EP | 1 793 004 | 6/2007 |
| EP | 1 854 883 | 11/2007 |
| EP | 2 180 062 | 4/2010 |
| WO | 02/31192 | 4/2002 |
| WO | 2006/028162 | 3/2006 |
| WO | 2006/093097 | 9/2006 |

OTHER PUBLICATIONS

The Stratagene Catalog p. 39 (1988).*
Supplementary European Search Report issued Dec. 21, 2010 in International (PCT) Application No. PCT/JP2008/064422.
Communication dated Jan. 7, 2011 in corresponding European Application No. 08827494.9 and Applicant's Response filed Jul. 18, 2011.
International Search Report issued Oct. 28, 2008 in International (PCT) Application No. PCT/JP2008/064422.
English translation of the International Preliminary Report on Patentability.

* cited by examiner

*Primary Examiner* — Ethan C Whisenant
(74) *Attorney, Agent, or Firm* — Wenderoth, Lind & Ponack, L.L.P.

(57) ABSTRACT

Provided are a method of detecting a target substance, by which the detection sensitivity in the PALSAR method can be improved and multiple genes can be simultaneously detected, and a kit for detection. The method is a method of detecting a target substance by forming a signal probe polymer with the use of multiple dimer probes or dimer-forming probes and an assist probe, in which each dimer probe is made up of two kinds of dimer-forming probes including a 5'-side region, a central region and a 3'-side region (the central regions of the two kinds of dimer-forming probes are complementary to each other and the 3'-side regions and the 5'-side regions thereof are not complementary to each other), the multiple dimer probes are constituted such that a dimer probe polymer is formed via a self-assembly reaction, and the assist probe is designed so as to have a structure having a region complementary to the 5'-side region of one dimer-forming probe in one dimer probe, a region complementary to the 3'-side region of the other dimer-forming probe, and a target region capable of binding to the target substance.

7 Claims, 5 Drawing Sheets

SEQUENCE LISTING

```
<160> NUMBER OF SEQ ID NOS: 16

<210> SEQ ID NO 1
<211> LENGTH: 42
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 1
catctctgct ggtccctcgg ctgcgtcggt tcgccataga cg            42

<210> SEQ ID NO 2
<211> LENGTH: 42
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 2
gcacattcac accgcgacgc agccgaggcc tgacctctat gc            42
```

```
<210> SEQ ID NO 3
<211> LENGTH: 42
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 3
gaccagcaga gatggcagcg acggcacccg tctatggcga ac                     42

<210> SEQ ID NO 4
<211> LENGTH: 42
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 4
cggtgtgaat gtgcggtgcc gtcgctgcgc atagaggtca gg                     42

<210> SEQ ID NO 5
<211> LENGTH: 105
<212> TYPE: DNA
<213> ORGANISM: Artificial
<220> FEATURE:
<223> OTHER INFORMATION: Description of Artificial Sequence; Synthetic

<400> SEQUENCE: 5
ttcgggaaac cggagctaat accggataat attttgaacc gcatggttca aaagtgaaag   60
acggtcttgc tgtcacttat agatggatcc gcgctgcatt agcta                 105

<210> SEQ ID NO 6
<211> LENGTH: 49
<212> TYPE: DNA
<213> ORGANISM: Artificial
<220> FEATURE:
<223> OTHER INFORMATION: Description of Artificial Sequence; Synthetic

<400> SEQUENCE: 6
gcatagaggt cagggaccag cagagatgat ctataagtga cagcaagac               49

<210> SEQ ID NO 7
<211> LENGTH: 42
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (42)..(42)
<223> OTHER INFORMATION: Aminolink attached at the 3'end

<400> SEQUENCE: 7
cgtctttcac ttttgaacca tgcggttcaa aatattatcc gg                     42

<210> SEQ ID NO 8
<211> LENGTH: 77
<212> TYPE: DNA
<213> ORGANISM: Artificial
<220> FEATURE:
<223> OTHER INFORMATION: Description of Artificial Sequence; Synthetic
```

```
<400> SEQUENCE: 8
gcatagaggt cagggaccag cagagatggc atagaggtca gggaccagca gagatgatct      60
ataagtgaca gcaagac                                                    77

<210> SEQ ID NO 9
<211> LENGTH: 77
<212> TYPE: DNA
<213> ORGANISM: Artificial
<220> FEATURE:
<223> OTHER INFORMATION: Description of Artificial Sequence; Synthetic

<400> SEQUENCE: 9
gttcgccata cacggcacat tcacaccggc atagaggtca gggaccagca gagatgatct      60
ataagtgaca gcaagac                                                    77

<210> SEQ ID NO 10
<211> LENGTH: 63
<212> TYPE: DNA
<213> ORGANISM: Artificial
<220> FEATURE:
<223> OTHER INFORMATION: Description of Artificial Sequence; Synthetic

<400> SEQUENCE: 10
catctctgct ggtccgtcta tggcgaaccg gtgtgaatgt gcatctataa gtgacagcaa      60
gac                                                                   63

<210> SEQ ID NO 11
<211> LENGTH: 63
<212> TYPE: DNA
<213> ORGANISM: Artificial
<220> FEATURE:
<223> OTHER INFORMATION: Description of Artificial Sequence; Synthetic

<400> SEQUENCE: 11
gaccagcaga gatgcgtcta tggcgaaccg gtgtgaatgt gcatctataa gtgacagcaa      60
gac                                                                   63

<210> SEQ ID NO 12
<211> LENGTH: 35
<212> TYPE: DNA
<213> ORGANISM: Artificial
<220> FEATURE:
<223> OTHER INFORMATION: Description of Artificial Sequence; Synthetic

<400> SEQUENCE: 12
gaccagcaga gatgatctat aagtgacagc aagac                                35

<210> SEQ ID NO 13
<211> LENGTH: 63
<212> TYPE: DNA
<213> ORGANISM: Artificial
<220> FEATURE:
<223> OTHER INFORMATION: Description of Artificial Sequence; Synthetic

<400> SEQUENCE: 13
catctctgct ggtccctcgg ctgcgtcggt tcgccataga cgatctataa gtgacagcaa      60
gac                                                                   63

<210> SEQ ID NO 14
<211> LENGTH: 63
<212> TYPE: DNA
<213> ORGANISM: Artificial
```

```
<220> FEATURE:
<223> OTHER INFORMATION: Description of Artificial Sequence; Synthetic

<400> SEQUENCE: 14
gaccagcaga gatgggtgcc gtcgctgccg tctatggcga acatctataa gtgacagcaa      60
gac                                                                   63

<210> SEQ ID NO 15
<211> LENGTH: 42
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 15
catctctgct ggtccctcgg ctgcgtcgag tgacagcaag ac                         42

<210> SEQ ID NO 16
<211> LENGTH: 42
<212> TYPE: DNA
<213> ORGANISM: Artificial
<220> FEATURE:
<223> OTHER INFORMATION: Description of Artificial Sequence; Synthetic
<220> FEATURE:
<221> NAME/KEY: misc_feature
<222> LOCATION: (1)..(1)
<223> OTHER INFORMATION: digoxigenin attached at the 5'end

<400> SEQUENCE: 16
gaccagcaga gatggcagcg acggcaccgt cttgctgtca ct                         42
```

METHOD OF DETECTING TARGET SUBSTANCE

This application is a U.S. national stage of International Application No. PCT/JP2008/064422 filed Aug. 11, 2008.

TECHNICAL FIELD

The present invention relates to a kit for detection of a target substance including multiple dimer probes which form a probe polymer and a novel assist probe, a method of detecting a target substance using the kit for detection, and a method of forming a signal probe polymer.

BACKGROUND ART

As a method of amplifying a signal without using an enzyme, Patent Document 1 discloses a method of amplifying a signal (hereinafter referred to as a PALSAR method), in which two sets of dimer probes, that is, a dimer probe having a structure of the following formula (1) and a dimer probe having a structure of the following formula (2) or (3), are used and an assembly substance (polymer) is formed by a self-assembly reaction of the dimer probes.

[Chemical Formula 1]

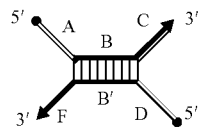

(1)

[Chemical Formula 2]

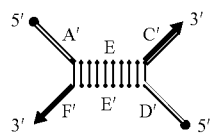

(2)

[Chemical Formula 3]

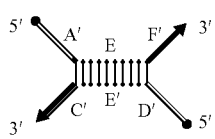

(3)

In the above formulae (1) to (3), a region A and a region A', a region B and a region B', a region C and a region C', a region D and a region D', a region E and a region E', and a region F and a region F' have complementary base sequences, respectively, and a self-assembly substance having a structure represented by the following formula (4) is formed by binding multiple dimer probes. The signal probe polymer as used, herein refers to a nucleic acid probe polymer including the self-assembly substance formed of the dimer probes.

[Chemical Formula 4]

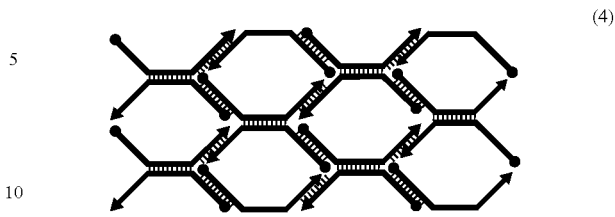

(4)

Patent Document 2 discloses a method of detecting a gene to be tested in a sample by using the above PALSAR method. Patent Document 2 discloses a method of detecting a gene to be tested with a high sensitivity by forming a complex of the gene to be tested and a probe polymer and detecting the probe polymer, and discloses a method of designing so that a part of one of multiple kinds of probes used for forming a polymer has a base sequence complementary to that of the gene to be tested, and a method of using a probe (an assist probe) having, at different site, both a base sequence complementary to that of the gene to be tested and a base sequence complementary to that of a probe used for forming a polymer as methods of forming a signal probe polymer on the gene to be tested. Note that the assist probe as used herein refers to a probe having both a region capable of binding to a target substance to be detected and a sequence complementary to that of a probe used for forming a polymer, and serves to connect the target substance with a signal probe polymer. A method of using the assist probe has an advantage in that multiple genes may be simultaneously detected with the same set of multiple kinds of probes by preparing multiple assist probes whose region complementary to a gene to be tested are different from each other.

Patent Document 2 describes an assist probe having a sequence complementary to one region of a dimer probe, but does not mention any study on an assist probe capable of detecting a target substance with high sensitivity.

Patent Document 1: WO 02/031192
Patent Document 2: WO 2006/028162

DISCLOSURE OF THE INVENTION

Problems to be Solved by the Invention

In the light of actual circumstances of the above-mentioned related arts, the inventors of the present invention have made extensive studies to allow the enhancement of the detection sensitivity in the PALSAR method also corresponding to simultaneous detection of multiple kinds of genes. As a result, the inventors have found a method of designing an assist probe suitable for the PALSAR method.

It is an object of the present invention to provide a method of detecting a target substance, the method allowing the enhancement of the detection sensitivity and simultaneous detection of multiple kinds of genes in the PALSAR method, a kit for detection including a dimer probe and an assist probe used for the method, and a method of forming a signal probe polymer using the assist probe, and a signal probe polymer formed by the method.

Means for Solving the Problems

The inventors of the present invention have made extensive studies on designs of an assist probe in order to solve the above-mentioned problem, and as a result, have found a method of designing an assist probe optimal for the PALSAR method, and have completed the present invention.

That is, the method of detecting a target substance of the present invention is characterized by including a method of detecting a target substance, including detecting a target substance by forming a signal probe polymer using multiple dimer probes or dimer-forming probes forming the dimer probes and an assist probe, in which: each dimer probe of the multiple dimer probes is a dimer formed of two kinds of dimer-forming probes, each dimer-forming probe includes three regions, i.e., a 5'-side region, a central region, and a 3'-side region, central regions of the two kinds of dimer-forming probes are complementary to each other, and 3'-side regions and 5'-side regions of the two kinds of dimer-forming probes are not complementary to each other, each 5'-side region in each dimer probe of the multiple dimer probes is complementary to a 5'-side region in any one of the other dimer probes, and each 3'-side region in each dimer probe of the multiple dimer probes is complementary to a 3'-side region in any one of the other dimer probes; and the assist probe has a region complementary to the 5'-side region in one dimer-forming probe in one dimer probe of the dimer probes, a region complementary to the 3'-side region in the other dimer-forming probe in the dimer probe, and a target region capable of binding to the target substance.

It is preferred that the dimer probes include two sets of dimer probes: a first dimer probe having a structure of the following formula (1); and a second dimer probe having a structure of the following formula (2) or (3), and the assist probe includes one or multiple sequences complementary to a region A and one or multiple sequences complementary to a region F in the following formula (1) or includes one or multiple sequences complementary to a region D and one or multiple sequences complementary to a region C in the following formula (1).

[Chemical Formula 5]

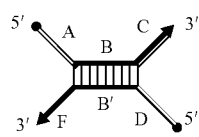

(1)

[Chemical Formula 6]

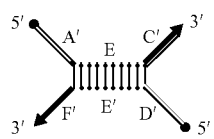

(2)

[Chemical Formula 7]

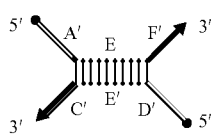

(3)

(in the above formulae (1) to (3), a region A and a region A', a region B and a region B', a region C and a region C', a region D and a region D', a region E and a region E', and a region F and a region F' have base sequences complementary to each other.)

The assist probe preferably includes one or more regions F'A' made up of the region F', and the region A' and a 3'-side in the region F' is preferably adjacent to a 5'-side in the region A' in the region F'A'.

Further, the assist probe suitably includes one or more regions C'D' made up of the region C' and the region D', and a 3'-side in the region C' is suitably adjacent to a 5'-side in the region D' in the region C'D'.

A method of forming a signal probe polymer of the present invention is characterized by including a method of forming a signal probe polymer, including reacting a target substance, multiple dimer probes or dimer-forming probes forming the dimer probes, and an assist probe, in which: each dimer probe in the multiple dimer probes is a dimer formed of two kinds of dimer-forming probes, each dimer-forming probe includes three regions, i.e., a 5'-side region, a central region, and a 3'-side region, central regions of the two kinds of dimer-forming probes are complementary to each other, and 3'-side regions and 5'-side regions of the two kinds of dimer-forming probes are not complementary to each other, each 5'-side region in each dimer probe of the multiple dimer probes is complementary to a 5'-side region in any one of the other dimer probes, and each 3'-side region in each dimer probe of the multiple dimer probes is complementary to a 3'-side region in any one of the other dimer probes; and the assist probe has a region complementary to the 5'-side region in one dimer-forming probe in one dimer probe of the dimer probes, a region complementary to the 3'-side region in the other dimer-forming probe in the dimer probe, and a target region capable of binding to the target substance.

The signal probe polymer of the present invention is characterized by being formed by the method of the present invention.

A kit for detection of a target substance of the present invention is characterized by including multiple dimer probes or dimer-forming probes forming the dimer probes and an assist probe, in which: each dimer probe of the dimer probes is a dimer formed of two kinds of dimer-forming probes, each dimer-forming probe includes three regions, i.e., a 5'-side region, a central region, and a 3'-side region, central regions of the two kinds of dimer-forming probes are complementary to each other, and 3'-side regions and 5'-side regions of the two kinds of dimer-forming probes are not complementary to each other, each 5'-side region in each dimer probe of the multiple dimer probes is complementary to a 5'-side region in any one of the other dimer probes, and each 3'-side region in each dimer probe of the multiple dimer probes is complementary to a 3'-side region in any one of the other dimer probes; and the assist probe has a region complementary to the 5'-side region in one dimer-forming probe in one dimer probe of the dimer probes, a region complementary to the 3'-side region in the other dimer-forming probe in the dimer probe, and a target region capable of binding to the target substance.

EFFECTS OF THE INVENTION

According to the present invention, it is possible to remarkably enhance the detection sensitivity in detecting a target substance using the PALSAR method. In addition, it is possible to simultaneously detect multiple target substances by changing a target region in the assist probe of the present invention.

DESCRIPTION OF SYMBOLS

10a: a first dimer probe, 10b, 10c, and 10d: second dimer probes, 10e: a third dimer probe, 11a to 11h, 11j, and 11k: dimer-forming probes, 12a to 12e: assist probes, 20: a target substance, 30: a signal probe polymer

BEST MODE FOR CARRYING OUT THE INVENTION

Hereinafter, embodiments of the present invention are described with reference to the accompanying drawings, which are for illustrative purposes only, and it will be appreciated that various variations may be made without departing from the technical idea of the present invention.

Figure 1:
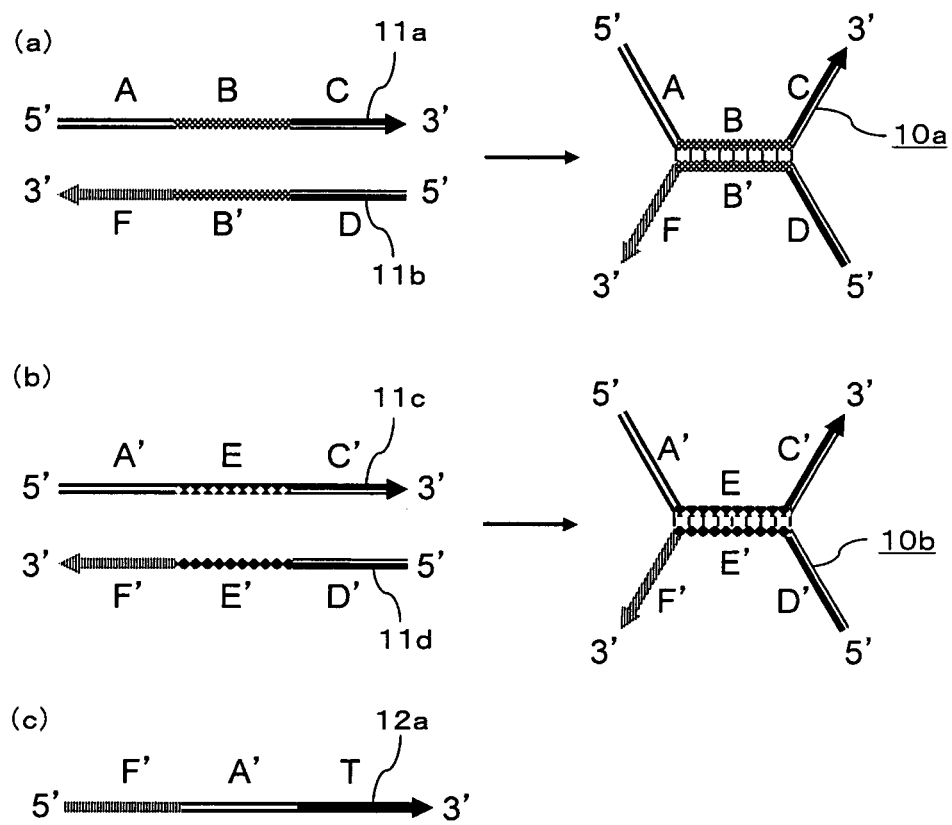
FIG. 1 is a schematic diagram illustrating one example of a kit for detection of the present invention, and first examples of a first dimer probe (a), a second dimer probe (b), and an assist probe (c) are illustrated.
Figure 2:
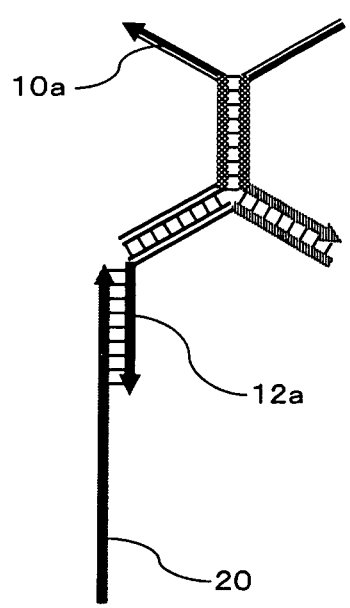
FIG. 2 is a schematic view illustrating a binding aspect of the dimer probe and a target substance to the assist probe described in FIG. 1.
Figure 3:
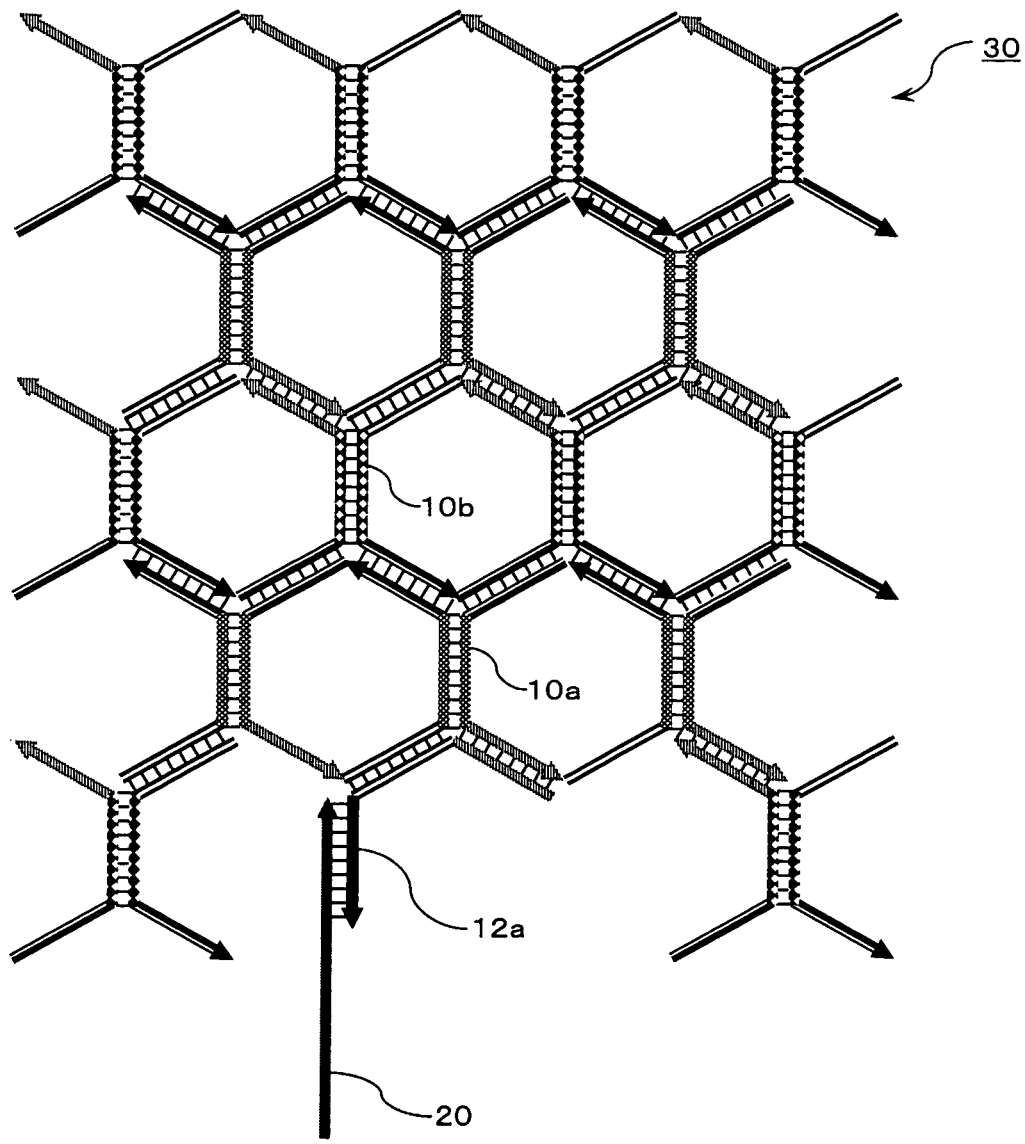
FIG. 3 is a schematic diagram illustrating one example of a method of forming a signal probe polymer using the kit for the detection described in FIG. 1.

FIG. 1 is a schematic diagram illustrating a first example of a kit for detection of a target substance of the present invention. FIG. 2 is a schematic diagram illustrating one example of binding aspects of a target substance, an assist probe, and a dimer probe in a method of forming a signal probe polymer using the kit for detection described in FIG. 1. FIG. 3 is a schematic diagram illustrating a formation of a signal probe polymer using the kit for detection described in FIG. 1.

The kit for the detection of a target substance of the present invention includes multiple dimer probes or dimer-forming probes forming the dimer probes and the assist probe.

The multiple dimer probes used in the present invention are constituted such that each 5'-side region in one dimer probe of the multiple dimer probes is complementary to a 5'-side region in any one of the other dimer probes and each 3'-side region in one dimer probe of the multiple dimer probes is complementary to a 3'-side region in any one of the other dimer probes, and can self-assemble to form a assembly substance (a probe polymer). For example, a nucleic acid probe described in Patent Document 1 is used.

FIGS. 1 to 3 illustrate one example of the case where two sets of dimer probes (a first dimer probe 10a and a second dimer probe 10b) are used.

As illustrated in FIG. 1(a), the first dimer probe 10a is formed by hybridizing two kinds of single strand nucleic acid probes (a first dimer-forming probe 11a and a second dimer-forming probe 11b). The first dimer-forming probe 11a includes three regions, i.e., a 5'-side region (a region A), a central region (a region B), and a 3'-side region (a region C). The second dimer-forming probe 11b includes three regions, i.e., a 5'-side region (a region D), a central region (a region B'), and a 3'-side region (a region F). In the first dimer-forming probe 11a and the second dimer-forming probe 11b, the central regions (regions B and B') are complementary to each other, and the 3'-side regions (regions C and F) and the 5'-side regions (regions A and F) are not complementary to each other.

As illustrated in FIG. 1(b), the second dimer probe 10b is formed by hybridizing two kinds of single strand nucleic acid probes (a third dimer-forming probe 11c and a fourth dimer-forming probe 11d). The third dimer-forming probe 11c includes three regions, i.e., the 5'-side region (a region A'), the central region (a region E), and the 3'-side region (a region C'). The fourth dimer-forming probe 11d includes three regions, i.e., the 5'-side region (a region D'), the central region (a region E'), and the 3'-side region (a region F'). In the third dimer-forming probe 11c and the fourth dimer-forming probe 11d, the central regions (regions E and E') are complementary to each other, and the 3'-side regions (regions C' and F') and the 5'-side regions (regions A' and F') are not complementary to each other.

Note that, as used herein, the region A' means a region having a base sequence complementary to the region A, the region C' means a region having a base sequence complementary to the region C, the region D' means a region having a base sequence complementary to the region D, and the region F' means a region having a base sequence complementary to the region F.

The 5'-side regions (regions A and D) in the first dimer probe 10a are complementary to the 5'-side regions (regions A' and D') in the second dimer probe 10b, and the 3'-side regions (regions C and F) in the first dimer probe 10a are complementary to the 3'-side regions (regions C' and F') in the second dimer probe 10b. A signal probe polymer 30 can be formed (FIG. 3) by hybridizing the first dimer probe 10a and the second dimer probe 10b.

In FIG. 1, the example in which the 5'-side region and the 3'-side region in the first dimer-forming probe 11a are complementary to the 5'-side region and the 3'-side region in the third dimer-forming probe 11c, respectively, and the 5'-side region and the 3'-side region in the second dimer-forming probe 11b are complementary to the 5'-side region and the 3'-side region in the fourth dimer-forming probe 11d, respectively is illustrated. However, in the present invention, the dimer probes just have to be constituted so that the 5'-side region in one dimer probe is complementary to the 5'-side region in the other dimer probe and the 3'-side region in one dimer probe is complementary to the 3'-side region in the other dimer probe.

Figure 4:
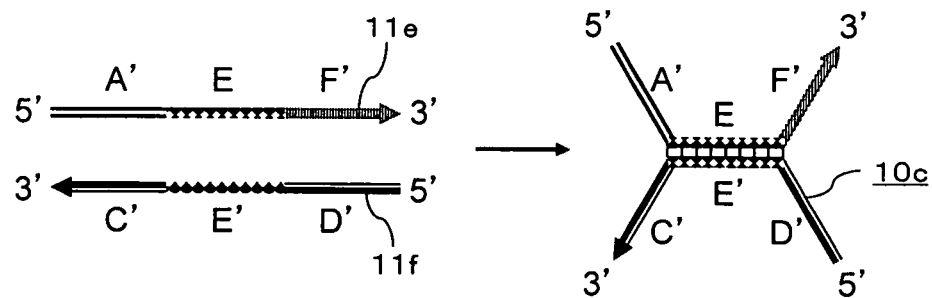
FIG. 4 is a schematic diagram illustrating another example of the second dimer probe.

FIG. 4 is a schematic diagram illustrating the other example of the second dimer probe to be used together with the first dimer probe 10a described in FIG. 1.

As illustrated in FIG. 4, a dimer probe 10c obtained by hybridizing a dimer-forming probe 11e, in which the 5'-side region is the region (a region A') complementary to the 5'-side region in the first dimer-forming probe 11a and the 3'-side region is the region (a region F') complementary to the 3'-side region in the second dimer-forming probe 11b with a dimer-forming probe 11f, in which the 5'-side region is the region (a region D') complementary to the 5'-side region in the second dimer-forming probe 11*b* and the 3'-side region is the region (a region C') complementary to the 3'-side region in the first dimer-forming probe 11*a* can also be used as the second dimer probe.

In FIG. 1, the example in which two kinds of dimer probes are used is shown, but if relative positions of the complementary regions are thought out, more kinds of dimer probes can be used (Patent Document 1).

Figure 13:
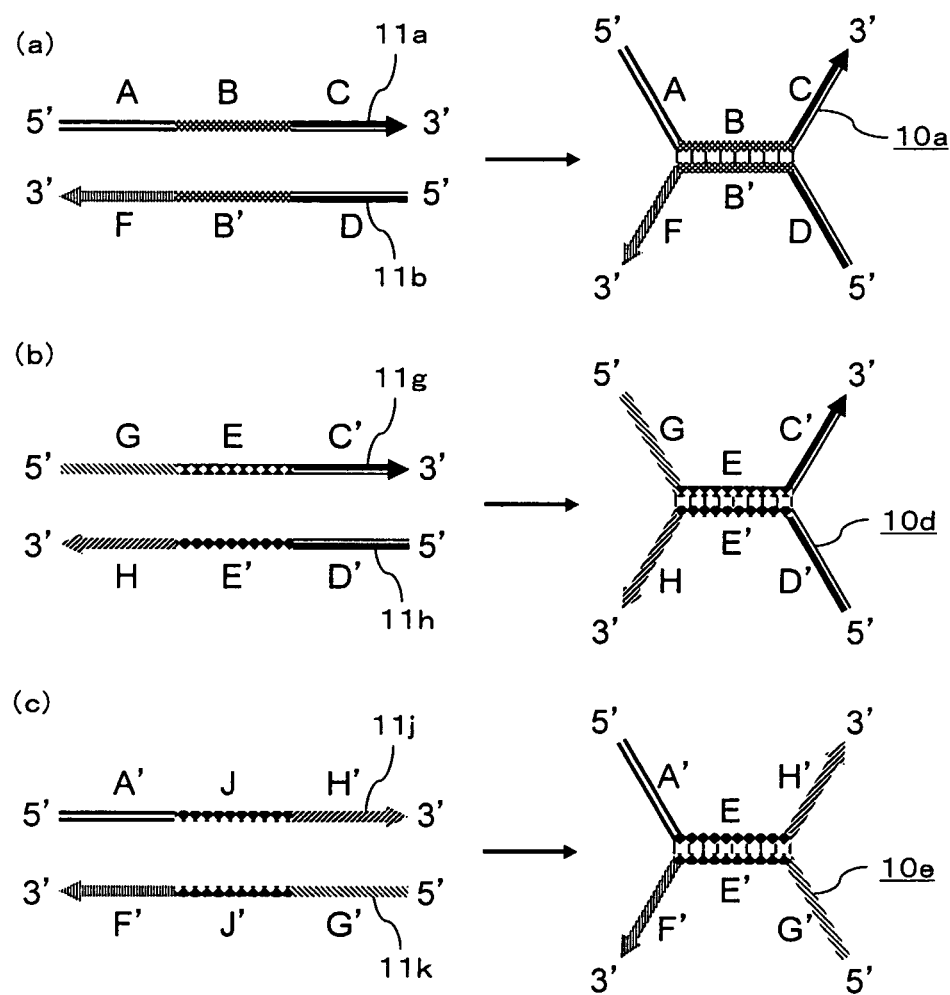
FIG. 13 is a schematic diagram illustrating another example of the dimer probe.

FIG. 13 is a schematic diagram illustrating one example of the case where three sets of dimer probes (a first dimer probe 10*a*, a second dimer probe 10*d* and a third dimer probe 10*e*) are used.

In FIG. 13(*a*), the first dimer probe 10*a* is constituted in the same way as in FIG. 1(*a*).

In FIG. 13(*b*), the second dimer probe 10*d* is formed by hybridizing two kinds of single strand nucleic acid probes (a dimer-forming probe 11*g* and a dimer-forming probe 11*h*). The dimer-forming probe 11*g* includes three regions, i.e., the 5'-side region (a region G), the central region (a region E), and the 3'-side region (a region C'), and the 3'-side region (a region C') is complementary to the 3'-side region (a region C) in the first dimer probe 10*a*. The dimer-forming probe 11*h* includes three regions, i.e., the 5'-side region (a region D'), the central region (a region E'), and the 3'-side region (a region H), and the 5'-side region (a region D') is complementary to the 5'-side region (a region D) in the first dimer probe 10*a*.

In FIG. 13(*c*), the third dimer probe 10*e* is formed by hybridizing two kinds of single strand nucleic acid probes (a dimer-forming probe 11*j* and a dimer-forming probe 11*k*). The dimer-forming probe 11*j* includes three regions, i.e., the 5'-side region (a region A'), the central region (a region J), and the 3'-side region (a region H'), and the 5'-side region (a region A') is complementary to the 5'-side region (a region A) in the first dimer probe 10*a*, and the 3'-side region (a region H') is complementary to the 3'-side region (a region H) in the second dimer probe 10*d*. The dimer-forming probe 11*k* includes three regions, i.e., the 5'-side region (a region G'), the central region (a region J'), and the 3'-side region (a region F'), and the 5'-side region (a region G') is complementary to the 5'-side region (a region G) in the second dimer probe 10*d*, and the 3'-side region (a region F') is complementary to the 3'-side region (a region. F) in the first dimer probe 10*a*. In the figure, the region J' is the region complementary to the region J.

That is, in FIG. 13, constitution is formed such that one 5'-side region and one 3'-side region in the first dimer probe are complementary to one 5'-side region and one 3'-side region in the second dimer probe, the other 5'-side region and the other 3'-side region in the first dimer probe are complementary to one 5'-side region and one 3'-side region in the third dimer probe, and the other 5'-side region and the other 3'-side region in the second dimer probe are complementary to the other 5'-side region and the other 3'-side region in the third dimer probe.

As illustrated in FIG. 13, the signal probe polymer which is the assembly substance of the dimer probes is formed by using multiple kinds of dimer probes constituted such that each 3'-side region in each dimer probe is complementary to the 3'-side region in any one of the other dimer probes and each 5'-side region in each dimer probe is complementary to the 5'-side region in any one of the other dimer probes and hybridizing these multiple kinds of dimer probes.

Note that, in the present invention, the combination of the dimer probes having complementary relations is not particularly limited, but it is preferred to be constituted such that one 3'-side region and one 5'-side region in each dimer probe are complementary to one 3'-side region and one 5'-side region, respectively, in the other one dimer probe as illustrated in FIG. 13.

The length of each complementary region in the dimer-forming probe is a length of at least 5 bases, preferably at least 8 bases, more preferably 10 to 100 bases, and still more preferably 12 to 30 bases. The lengths of the complementary regions in the respective probes are desirably the same as each other.

The base sequence in each region of the dimer-forming probe is not particularly limited as long as the sequence is constituted in such a manner that the predetermined region has the complementary sequence so that the dimer probe of the present invention is formed, and it is preferred that the bases at both ends in each region be guanine or cytosine. By making the bases at both ends in each region guanine or cytosine, a reaction time can be shortened, and further, a stable probe polymer can be formed at lower reaction temperatures, to thereby enhance the workability and detection sensitivity.

The assist probe of the present invention has a region complementary to the 5'-side region in one dimer-forming probe in one dimer probe of the dimer probes, a region complementary to the 3'-side region in the other dimer-forming probe in the dimer probe, and a target region capable of binding to a target substance, and is bound to two single strand regions at one end of at least one dimer probe.

FIG. 1(*c*) illustrates one example of the assist probe of the present invention. In FIG. 1(*c*), a first example of the assist probe of the present invention is represented by 12*a*, and the assist probe has a region (a region A') having a sequence complementary to the 5'-side region (a region A) in the first dimer-forming probe 11*a* of the dimer probe 10*a*, a region (a region F') having a sequence complementary to the 3'-side region (a region F) in the second dimer-forming probe 11*b* of the dimer probe 10*a*, and a target region (a region T) capable of binding to a target substance. In the assist probe 12*a*, the 3'-side of the region F' is adjacent to the 5'-side of the region A'.

In the assist probe of the present invention, the relative position of each region is not particularly limited, but as illustrated in FIG. 1, it is preferred that the regions to be bound to the dimer probe be adjacent. It is more preferred that a 5'-side of one region (e.g., a region A') complementary to the 5'-side region in one dimer-forming probe in the dimer probe be adjacent to a 3'-side of one region (e.g., a region F') complementary to the 3'-side region of the other dimer-forming probe in the dimer probe.

Specifically, when two sets of dimer probes (10*a*, 10*b*) described in FIG. 1 are used, it is preferred that the assist probe includes one or more regions selected from the group consisting of a region F'A' (a region made up of the region F' and the region A' and in which the 3'-side of the region F' is adjacent to the 5'-side of the region A'), a region C'D' (a region made up of the region C' and the region D' and in which the 3'-side of the region C' is adjacent to the 5'-side of the region D'), a region FA (a region made up of the region F and the region A and in which the 3'-side of the region F is adjacent to the 5'-side of the region A), and a region CD (a region made up of the region C and the region D and in which the 3'-side of the region C is adjacent to the 5'-side of the region D). When the dimer probe 10*c* described in FIG. 4 is used as the second dimer probe, it is preferred to use the assist probe including one or more regions selected from the group consisting of the region F'A', the region C'D', a region CA (a region made up of the region C and the region A and in which the 3'-side of the region C is adjacent to the 5'-side of the region A), and a region FD (a region made up of the region F and the region D and in which the 3'-side of the region F is adjacent to the 5'-side of the region D). By making such a constitution, as illustrated in FIG. 2, the assist probe can be bound consecutively to the two single strand regions at one end in one dimer probe and detect the target substance with the high sensitivity.

In FIGS. 1 to 3, the example in which by using the assist probe 12a made up of the region F'A' and the region T, the region F'A' in the assist probe 12a is bound consecutively to the two single strand regions (regions F and A) at one end of one first dimer probe 10a and the region T is bound to the target substance 20 is shown, but in the present invention, the dimer probe to be bound to the assist probe is not particularly limited as long as the dimer probe is appropriately selected from the dimer probes to be used.

The target region may be appropriately selected depending on a target substance in the assist probe of the present invention. When the target substance is a nucleic acid, it is preferred to adopt such a structure that the target region has a base sequence complementary to a target nucleic acid. When the target substance is a protein such as an antigen, it is preferred that a substance such as an antibody specifically binding to the target substance be bound directly or indirectly. Note that FIG. 2 illustrates an example in which the assist probe 12a is directly bound to a target substance 20, but the assist probe 12a may be bound indirectly to the target substance 20 via other nucleic acid probes and the like.

It is preferred that the target region (a region T) be located at the end portion in the assist probe. Note that FIG. 1 illustrates an example in which the target region (a region T) is formed at the 3' end, but the target region (a region T) may be formed at the 5' end.

As illustrated in FIG. 3, the signal probe polymer 30 made up of a complex including a polymer formed of two sets of the dimer probes 10a and 10b, and the assist probe 12a, and the target substance 20 is formed by reacting two sets of the dimer probes (symbols 10a and 10b), the assist probe 12a, and the target substance 20 each described in FIG. 1.

In the present invention, the dimer probe, the assist probe, and the target substance can be reacted simultaneously, but it is preferred that the target substance be reacted with the assist probe and subsequently the dimer probe be reacted with the reaction product.

In the present invention, the dimer-forming probes before forming the dimer probe may be used in place of the dimer probe, but it is preferred to use the dimer probe.

The target substance 20 can be detected by detecting the formed signal probe polymer 30.

The method of detecting a signal probe polymer is not particularly limited, but it is suitable to detect the signal probe polymer by using the dimer probe labeled with a labeling substance and detecting the labeling substance. The labeling substance includes, for example, a radioisotope, biotin, digoxigenin, a fluorescent substance, a luminescent substance, and a dyestuff as suitable examples. An intercalator such as ethidium bromide, OliGreen, and SYBR Green I may be bound to the formed signal probe polymer, and detected with fluorescence and the like.

Figure 5:
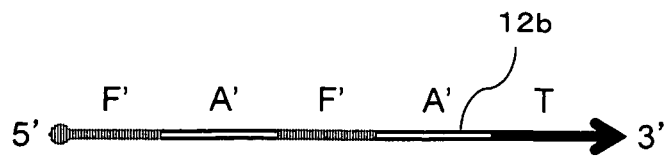
FIG. 5 is a schematic diagram illustrating a second example of the assist probe.
Figure 6:
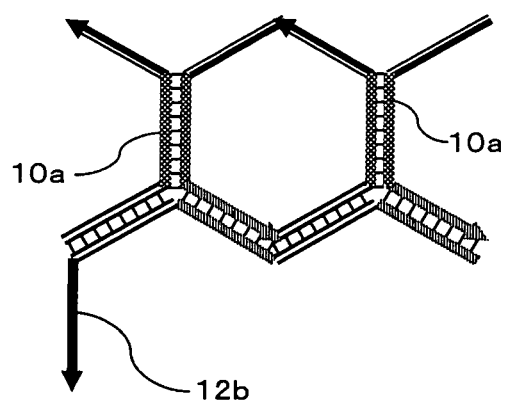
FIG. 6 is a schematic view illustrating the binding aspect of the dimer probe to the assist probe described in FIG. 5.
Figure 7:
FIG. 7 is a schematic diagram illustrating a third example of the assist probe.
Figure 8:
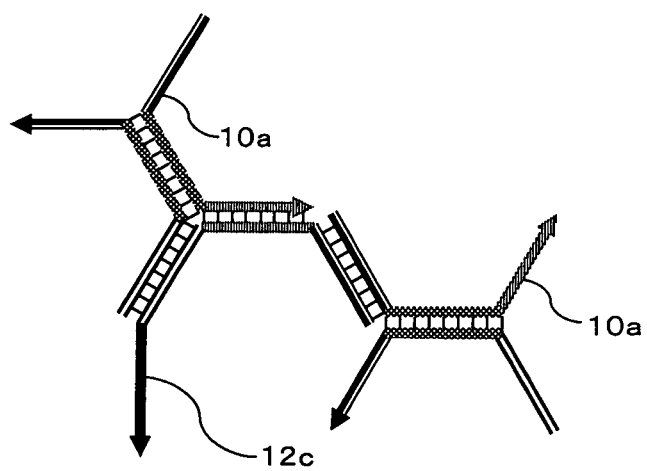
FIG. 8 is a schematic view illustrating the binding aspect of the dimer probe to the assist probe described in FIG. 7.
Figure 9:
FIG. 9 is a schematic diagram illustrating a fourth example of the assist probe.
Figure 10:
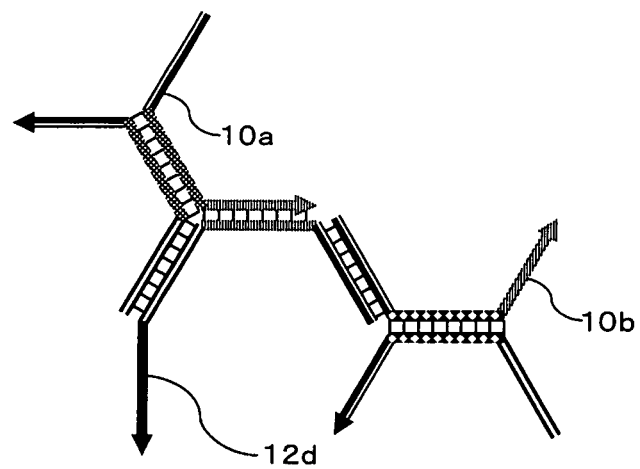
FIG. 10 is a schematic view illustrating the binding aspect of the dimer probe to the assist probe described in FIG. 9.
Figure 11:
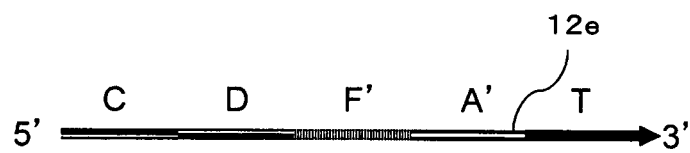
FIG. 11 is a schematic diagram illustrating a fifth example of the assist probe.
Figure 12:
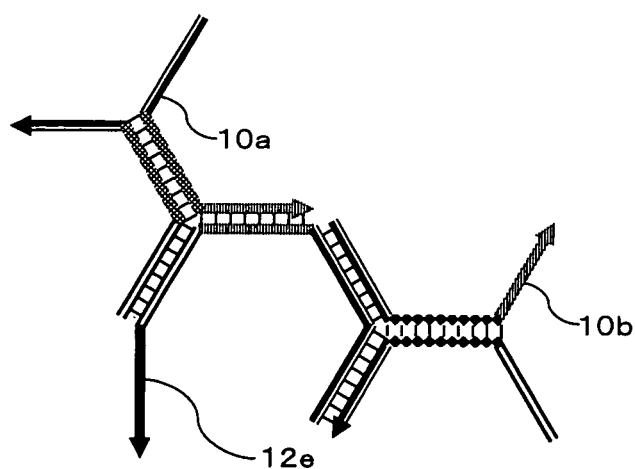
FIG. 12 is a schematic view illustrating the binding aspect of the dimer probe to the assist probe described in FIG. 11.

FIG. 5 is a schematic diagram illustrating a second example of the assist probe to be used together with the two sets of dimer probes described in FIG. 1, and FIG. 6 is a schematic view illustrating the binding aspect of the dimer probes to the assist probe described in FIG. 5. FIG. 7 is a schematic diagram illustrating a third example of the assist probe to be used together with the two sets of dimer probes described in FIG. 1, and FIG. 8 is a schematic view illustrating the binding aspect of the dimer probes to the assist probe described in FIG. 7. FIG. 9 is a schematic diagram illustrating a fourth example of the assist probe to be used together with the two sets of dimer probes described in FIG. 1, and FIG. 10 is a schematic view illustrating the binding aspect of the dimer probes to the assist probe described in FIG. 9. FIG. 11 is a schematic diagram illustrating a fifth example of the assist probe to be used together with the two sets of dimer probes described in FIG. 1, and FIG. 12 is a schematic view illustrating the binding aspect of the dimer probes to the assist probe described in FIG. 11.

The assist probe of the present invention includes one or more regions complementary to the single strand region in the dimer probes to be used, in addition to one region complementary to the 5'-side region in one dimer-forming probe in the dimer probe, one region complementary to the 3'-side region in the other dimer-forming probe in the dimer probe, and the target region capable of binding to the target substance, thereby being capable of binding one assist probe to two or more dimer probes.

Examples of the assist probe binding to two dimer probes are illustrated in FIGS. 5 to 12. In FIGS. 5 to 12, the assist probes 12b to 12e are constituted such that one or more additional regions (a region A', C', D', F', A, C, D, or F) complementary to the single strand regions (a region A, C, D, F, A', C', D', or F') of the dimer probe are further added to the assist probe 12a described in FIG. 1, i.e., are constituted so as to have one or more additional regions in addition to the region F'A' complementary to two regions at one end in the first dimer probe 10a and capable of binding consecutively to the two regions and the target region T capable of binding to the target substance, and are constituted such that the target region T is located at the end region in the assist probe.

When one assist probe is bound to two or more dimer probes, the combination of the dimer probes is not particularly limited. For example, two or more of dimer probes of one kind may be bound as illustrated in FIGS. 5 to 8, or different kinds of dimer probes may be combined and bound as illustrated in FIGS. 9 to 12. In FIGS. 5 to 12, the examples in which two regions (Regions F'A') complementary to 2 regions (regions A and F) at one end in the first dimer probe 10a are selected as essential two regions to be bound to the dimer probe is shown, but in the present invention, the dimer probe to be bound to the assist probe is not particularly limited as long as the dimer probe is appropriately selected from the dimer probes to be used.

The number and kind of the additional regions in the assist probe are not particularly limited. For example, the additional region in the assist probe may be one region as illustrated in FIGS. 7 and 9 and may be bound to one region in the dimer probe as illustrated in FIGS. 8 and 10. However, it is preferred that the additional regions in the assist probe be two or more regions including one or more of two regions (e.g., regions F'A', regions C'D', regions FA, and regions CD,) capable of binding to two regions at one end in the dimer probe as illustrated in FIGS. 5 and 11, and be bound consecutively to the two regions at the one end in the dimer probe as illustrated in FIGS. 6 and 12.

It is preferred that the assist probe of the present invention alternately includes two regions (e.g., a region F' and a region A') complementary to two regions at one end in the dimer probe as illustrated in FIGS. 5 and 6. By making such a constitution, one assist probe can be bound alternately and consecutively to the two regions at the same end side in the same kind of the dimer probe, and can detect the target substance with extremely high sensitivity. In the sequence alternately including two regions complementary to two regions at one end in the dimer probe, an initial region and a last region can be selected from either the two regions, but it is preferred to constitute the assist probe so as to include multiple times of the regions (e.g., regions F'A', regions C'D', regions FA, and regions CD) capable of being consecutively bound to two regions at one end in the dimer probe as illustrated in FIGS. 5 and 6.

In the method of detecting a target substance of the present invention, it is preferred to use a carrier to which a substance capable of capturing a target substance has been immobilized. For example, when the target substance is a nucleic acid, it is preferred to use a nucleic acid probe having the sequence complementary to a site different from a binding site with the assist probe as a capture probe and use a carrier on the surface of which the capture probe has been immobilized. It is suitable to constitute the carrier such that the assist probe and the capture probe in an adjacent state are bound to the target nucleic acid.

As the carrier, it is preferred to use, for example, a fluorescent fine particle, a magnetic particle, a microplate, a microarray, a slide glass, and a substrate such as an electrically conductive substrate.

In the present invention, by combining multiple assist probes having different target regions T, it is possible to simultaneously detect multiple kinds of target substances. In the simultaneous detection of multiple kinds of target substances, the same dimer probes can be used, multiple kinds of assist probes and carriers capturing the target substance have only to be prepared, and thus the simultaneous detection is excellent in workability and low in cost.

EXAMPLES

Hereinafter, the present invention is described more specifically by way of examples, but it goes without saying that those examples are for illustrative purposes only and should not be construed as restrictive ones.

Example 1

Two kinds of dimer probe described in FIG. 1 were used as the dimer probe. As nucleic acid probes used for forming the dimer probe, four kinds of oligonucleotide probes (a first dimer-forming probe-1, a second dimer-forming probe-1, a third dimer-forming probe-1, and a fourth dimer-forming probe-1) having the following base sequences, 5' ends of which had been labeled with digoxigenin, were used.

```
Base sequence of first dimer-forming probe-1
(5'-ABC-3')
                                      (SEQ ID NO: 1)
5'-DIG-CATCTCTGCTGGTC CCTCGGCTGCGTCG

GTTCGCCATAGACG-3'

Base sequence of second dimer-forming probe-1
(5'-DB'F-3')
                                      (SEQ ID NO: 2)
5'-DIG-GCACATTCACACCG CGACGCAGCCGAGG

CCTGACCTCTATGC-3'

Base sequence of third dimer-forming probe-1
(5'-A'EC'-3')
                                      (SEQ ID NO: 3)
5'-DIG-GACCAGCAGAGATG GCAGCGACGGCACC

CGTCTATGGCGAAC-3'
```

```
Base sequence of fourth dimer-forming probe-1
(5'-D'E'F'-3')
                                      (SEQ ID NO: 4)
5'-DIG-CGGTGTGAATGTGC GGTGCCGTCGCTGC

GCATAGAGGTCAGG-3'
```

The first dimer-forming probe-1 and the second dimer-forming probe-1 each were dissolved at a final concentration of 500 pmol/mL in a solution [4×SSC, 0.2% SDS, 1% blocking reagent (manufactured by Roche)]. Subsequently the solution was heated at 94° C. for 1 minute and reacted at 60° C. for 2 hours to prepare a first dimer probe solution.

In addition, the third dimer-forming probe-1 and the fourth dimer-forming probe-1 each were dissolved at a final concentration of 500 pmol/mL in a solution [4×SSC, 0.2% SDS, 1% blocking reagent (manufactured by Roche)]. Subsequently the solution was heated at 94° C. for 1 minute and reacted at 60° C. for 2 hours to prepare a second dimer probe solution.

A synthesized DNA (a target oligo DNA) having the same base sequence as a rRNA from Staphylococcus aureus was used as a target substance.

```
Base sequence of target oligo DNA
                                      (SEQ ID NO: 5)
5'-TTCGGGAAACCGGAGCTAATACCGGATAATATTTTGAACCGCATGGT

TCAAAAGTGAAAGACGGTCTTGCTGTCACTTATAGATGGATCCGCGCTGC

ATTAGCTA-3'
```

A nucleic acid probe (an assist probe-1, an assist probe described in FIG. 1) having a region complementary to a 3'-side region of the second dimer-forming probe, a region complementary to a 5'-side region of the second dimer-forming probe, and a region complementary to the target oligo DNA sequentially from the 5'-side was used as the assist probe.

```
Base sequence of assist probe-1 (5'-F'A'-T₁-3')
                                      (SEQ ID NO: 6)
5'-GCATAGAGGTCAGG GACCAGCAGAGATG ATCTATAAGTGACAGCA

AGAC-3'
```

The assist probe-1 was dissolved at a final concentration of 25 pmol/mL in a solution [4×SSC, 0.2% SDS, 1% blocking reagent (manufactured by Roche), 20% formaldehyde, salmon sperm DNA (10 μg/mL)] to prepare an assist probe solution.

A nucleic acid probe having the sequence complementary to the target oligo DNA was used as a capture probe.

```
Base sequence of capture probe
                                      (SEQ ID NO: 7)
5'-CGTCTTTCACTTTTGAACCATGCGGTTCAAAATATTATCCGG-3'-

Amino link
```

The capture probe was immobilized in each of the wells in a strip well type 96-well microplate, which was then used for an experiment.

Subsequently, 50 μL, of the target oligo DNA at each concentration (0.1, 1, or 10 fmol/mL) and 50 μL, of the assist probe solution were added to the strip well type 96-well microplate prepared above, the microplate was tightly sealed with a plate sealer, and the contents in the microplate were reacted under a condition, at 20° C. in the upper part and 55° C. in the lower part of the microplate, for 45 minutes. After the reaction, the microplate was washed with a washing solution [50 mM Tris, 0.3 M NaCl, 0.01% Triton X-100, pH 7.6].

After washing, the washing solution was drained well, and 25 µL of a first dimer probe solution, 25 µL of a second dimer probe solution, and 50 µL of a solution [4×SSC, 0.2% SDS, 1% blocking reagent (manufactured by Roche)] were added to the 96-well microplate, which was then tightly sealed with a plate sealer. The contents in the microplate were reacted under the condition, at 20° C. in the upper part and 55° C. in the lower part of the microplate, for 30 minutes, and the microplate was then washed with a washing solution.

After washing the microplate well, 100 µL of 15 mU/mL of ALP-labeled anti-digoxigenin (100 mM Tris, pH 7.5) were added to the microplate, followed by reaction in an incubator at 37° C. After washing the microplate, 100 µL of a luminescent substrate solution (CDP-Star manufactured by TROPIX) were added to the microplate, and after reaction in a dark place for 20 minutes, a luminescence intensity (RLU) was measured using a luminometer (Centro LB960 manufactured by Berthold). Results are shown in Table 1.

Example 2

An experiment was carried out in the same way as in Example 1, except that an assist probe-2 having the following base sequence was used as the assist probe in place of the assist probe-1. The results are shown in Table 1.

```
Base sequence of assist probe-2
(5'-F'A'-F'A'-T₁-3')
                                    (SEQ ID NO: 8)
5'-GCATAGAGGTCAGG GACCAGCAGAGATG GCATAGAGGTCAGG

GACCAGCAGAGATGATCTATAAGTGACAGCAAGAC-3'
```

Example 3

An experiment was carried out in the same way as in Example 1, except that an assist probe-3 having the following base sequence was used as the assist probe in place of the assist probe-1. The results are shown in Table 1.

```
Base sequence of assist probe-3 (5'-CD-F'A'-T₁-3')
                                    (SEQ ID NO: 9)
5'-GTTCGCCATAGACG GCACATTCACACCG GCATAGAGGTCAGG

GACCAGCAGAGATGATCTATAAGTGACAGCAAGAC-3'
```

Example 4

An experiment was carried out in the same way as in Example 1, except that an assist probe-4 having the following base sequence was used as the assist probe in place of the assist probe-1. The results are shown in Table 1.

```
Base sequence of assist probe-4 (5'-A-C'D'-T₁-3')
                                    (SEQ ID NO: 10)
5'-CATCTCTGCTGGTC CGTCTATGGCGAAC CGGTGTGAATGTGC

ATCTATAAGTGACAGCAAGAC-3'
```

Example 5

An experiment was carried out in the same way as in Example 1, except that an assist probe-5 having the following base sequence was used as the assist probe in place of the assist probe-1. The results are shown in Table 1.

```
Base sequence of assist probe-5 (5'-A'-C'D'-T₁-3')
                                    (SEQ ID NO: 11)
5'-GACCAGCAGAGATG CGTCTATGGCGAAC CGGTGTGAATGTGC

ATCTATAAGTGACAGCAAGAC-3'
```

Experimental Example 1

An experiment was carried out in the same way as in Example 1, except that a nucleic acid probe (an assist probe-6) having the region complementary to the 5'-side region in the first dimer-forming probe-1, and the region complementary to the target oligo DNA was used as the assist probe in place of the assist probe-1. The results are shown in Table 1.

```
Base sequence of assist probe-6 (5'-A'-T₁-3')
                                    (SEQ ID NO: 12)
5'-GACCAGCAGAGATG ATCTATAAGTGACAGCAAGAC-3'
```

Experimental Example 2

An experiment was carried out in the same way as in Example 1, except that a nucleic acid probe (an assist probe-7) having unexceptionally the same base sequence as the first dimer-forming probe-1 (i.e., made up of the region complementary to the 5'-side region in the third dimer-forming probe-1, the region which was not bound to the dimer probe, and the region complementary to the 3'-side region in the third dimer-forming probe-1) and the region complementary to the target oligo DNA was used as the assist probe in place of the assist probe-1. The results are shown in Table 1.

```
Base sequence of assist probe-7 (5'-ABC-T₁-3')
                                    (SEQ ID NO: 13)
5'-CATCTCTGCTGGTC CCTCGGCTGCGTCG GTTCGCCATAGACG

ATCTATAAGTGACAGCAAGAC-3'
```

Experimental Example 3

An experiment was carried out in the same way as in Example 1, except that a nucleic acid probe (an assist probe-8) having unexceptionally the same base sequence as the third dimer-forming probe-1 (i.e., made up of the region complementary to the 5'-side region in the first dimer-forming probe-1, the region which was not bound to the dimer probe, and the region complementary to the 3'-side region in the first dimer-forming probe-1) and the region complementary to the target oligo DNA was used as the assist probe in place of the assist probe-1. The results are shown in Table 1.

```
Base sequence of assist probe-8 (5'-A'EC'-T₁-3')
                                    (SEQ ID NO: 14)
5'-GACCAGCAGAGATG GGTGCCGTCGCTGC CGTCTATGGCGAAC

ATCTATAAGTGACAGCAAGAC-3'
```

Experimental Example 4

An experiment was carried out using a dimer probe having the sequence complementary to the target oligo DNA.

A first dimer probe solution was prepared in the same way as in Example 1, except that a first dimer-forming probe-2 having the following base sequence, 5' end of which had been labeled with digoxigenin, was used in place of the first dimer-forming probe-1.

```
Base sequence of first dimer-forming probe-2
(5'-AB-T2-3')
                                         (SEQ ID NO: 15)
5'-DIG-CATCTCTGCTGGTC CCTCGGCTGCGTCG AGTGACAGCAAGA

C-3'
```

A second dimer probe solution was prepared in the same way as in Example 1, except that a third dimer-forming probe-2 having the following base sequence, 5' end of which had been labeled with digoxigenin, was used in place of the third dimer-forming probe-1.

```
Base sequence of the third dimer-forming probe-2
(5'-A'E-T2'-3')
                                         (SEQ ID NO: 16)
5'-DIG-GACCAGCAGAGATG GCAGCGACGGCACC GTCTTGCTGTCAC

T-3'
```

An experiment was carried out in the same way as in Example 1, except that a solution [4×SSC, 0.2% SDS, 1% blocking reagent (manufactured by Roche), 20% formamide, salmon sperm DNA (10 μg/mL)] containing no assist probe was used in place of the assist probe solution and further, the first and second dimer probe solutions were changed as described above. The results are shown in Table 1.

Experimental Example 5

An experiment was carried out in the same way as in Example 1, except that a solution [4×SSC, 0.2% SDS, 1% blocking reagent (manufactured by Roche), 20% formamide, salmon sperm DNA (10 μg/mL)] containing 25 μmol/mL of the first dimer-forming probe-2 described in Experimental Example 4 was used in place of the assist probe solution and further, the first and the second dimer probe solutions were changed in the same way as in Experimental Example 4. The results are shown in Table 1.

TABLE 1

|  | Target oligo DNA concentration (fmol/mL) | | |
| --- | --- | --- | --- |
|  | 0.1 | 1 | 10 |
| Example 1 | 989 | 10,565 | 81,457 |
| Example 2 | 1,438 | 14,452 | 95,239 |
| Example 3 | 1,545 | 13,513 | 98,221 |
| Example 4 | 1,044 | 10,329 | 62,865 |
| Example 5 | 888 | 8,425 | 61,555 |
| Experimental Example 1 | 175 | 1,529 | 14,353 |
| Experimental Example 2 | 531 | 5,446 | 45,347 |
| Experimental Example 3 | 509 | 4,484 | 35,162 |
| Experimental Example 4 | 411 | 4,394 | 37,702 |
| Experimental Example 5 | 450 | 4,676 | 36,746 |

As shown in Table 1, the detection sensitivity in Examples 1 to 5 using the assist probe of the present invention was remarkably enhanced.

The invention claimed is:

1. A method of detecting a target substance, comprising:
contacting the target substance with an assist probe and a plurality of pairs of dimer-forming probes, and
detecting a signal probe polymer formed of the plurality of pairs of dimer-forming probes, the assist probe and the target substance, wherein the detection of said signal probe polymer indicates the presence of said target substsance in a sample,
wherein:
the plurality of pairs of dimer-forming probes comprise at least a first pair of dimer- forming probes and a second pair of dimer-forming probes,
each dimer-forming probe of the first pair of dimer-forming probes, and each dimer-forming probe of the second pair of dimer-forming probes, comprises a 5'-side region, a central region, and a 3'-side region,
the central regions of the dimer-forming probes of the first pair of dimer-forming probes are complementary to each other, and the central regions of the dimer-forming probes of the second pair of dimer-forming probes are complementary to each other,
the 3'-side regions of the dimer-forming probes of the first pair of dimer-forming probes are different from each other and not complementary to the opposing 5'-side regions of the dimer-forming probes of the first pair of dimer-forming probes,
the 3'-side regions of the dimer-forming probes of the second pair of dimer-forming probes are different from each other and not complementary to the opposing 5'-side regions of the dimer-forming probes of the second pair of dimer-forming probes,
the 5'-side regions of the dimer-forming probes of the first pair of dimer-forming probes are complementary to the 5'-side regions of the dimer-forming probes of the second pair of dimer-forming probes,
the 3'-side regions of the dimer-forming probes of the first pair of dimer-forming probes are complementary to the 3'-side regions of the dimer-forming probes of the second pair of dimer-forming probes,
the assist probe has a region complementary to a 5'-side region of a dimer-forming probe of the first pair of dimer-forming probes, a region complementary to an opposing 3'-side region of the dimer-forming probe of the first pair of dimer-forming probes, and a target region capable of binding to the target substance, and
the target substance, assist probe and the plurality of pairs of dimer-forming probes are nucleic acids.

2. The method of detecting a target substance according to claim 1, wherein
the first pair of dimer-forming probes forms a first dimer probe, and the second pair of dimer-forming probes forms a second dimer probe,
the first dimer probe has a structure of the following Chemical Formula 1 and the second dimer probe has a structure of the following Chemical Formula 2 or Chemical Formula 3,

[Chemical Formula 1]

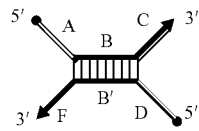

(1)

[Chemical Formula 2]

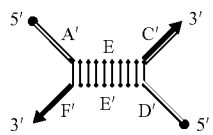

(2)

[Chemical Formula 3]

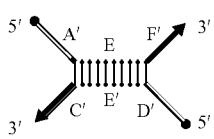

(3)

wherein:
in the Chemical Formulae 1, 2 and 3, a region A and a region A' have base sequences complementary to each other, a region B and a region B' have base sequences complementary to each other, a region C and a region C' have base sequences complementary to each other, a region D and a region D' have base sequences complementary to each other, a region E and a region E' have base sequences complementary to each other, and a region F and a region F' have base sequences complementary to each other, and
the assist probe comprises one or more sequences complementary to a region A and one or more sequences complementary to a region F in the Chemical Formula 1, or the assist probe comprises one or more sequences complementary to a region D and one or more sequences complementary to a region C in the Chemical Formula 1.

3. The method of detecting a target substance according to claim 2, wherein the assist probe comprises one or more regions F'A' comprising the region F' and the region A' of the Chemical Formula 2 or the Chemical Formula 3, wherein a 3'-side in the region F' is adjacent to a 5'-side in the region A' in the region F'A'.

4. The method of detecting a target substance according to claim 2, wherein the assist probe comprises one or more regions C'D' comprising the region C' and the region D' of the Chemical Formula 2 or the Chemical Formula 3, wherein a 3'-side in the region C' is adjacent to a 5'-side in the region D' in the region C'D'.

5. A method of forming a signal probe polymer, comprising contacting a target substance with an assist probe and a plurality of pairs of dimer-forming probes, thereby forming said signal probe polymer,
wherein:
the plurality of pairs of dimer-forming probes comprise at least a first pair of dimer-forming probes and a second pair of dimer-forming probes,
each dimer-forming probe of the first pair of dimer-forming probes, and each dimer-forming probe of the second pair of dimer-forming probes, comprises a 5'-side region, a central region, and a 3'-side region,
the central regions of the dimer-forming probes of the first pair of dimer-forming probes are complementary to each other, and the central regions of the dimer-forming probes of the second pair of dimer-forming probes are complementary to each other,
the 3'-side regions of the dimer-forming probes of the first pair of dimer-forming probes are different from each other and not complementary to the opposing 5'-side regions of the dimer-forming probes of the first pair of dimer-forming probes,
the 3'-side regions of the dimer-forming probes of the second pair of dimer-forming probes are different from each other and not complementary to the opposing 5'-side regions of the dimer-forming probes of the second pair of dimer-forming probes,
the 5'-side regions of the dimer-forming probes of the first pair of dimer-forming probes are complementary to the 5'-side regions of the dimer-forming probes of the second pair of dimer-forming probes,
the 3'-side regions of the dimer-forming probes of the first pair of dimer-forming probes are complementary to the 3'-side regions of the dimer-forming probes of the second pair of dimer-forming probes,
the assist probe has a region complementary to a 5'-side region of a dimer-forming probe of the first pair of dimer-forming probes, a region complementary to an opposing 3'-side region of the dimer-forming probe of the first pair of dimer-forming probes, and a target region capable of binding to the target substance, and
the target substance, assist probe and the plurality of pairs of dimer-forming probes are nucleic acids.

6. A signal probe polymer, which is obtained by reacting a target substance, a plurality of pairs of dimer-forming probes, and an assist probe,
wherein:
the plurality of pairs of dimer-forming probes comprise at least a first pair of dimer-forming probes and a second pair of dimer-forming probes,
each dimer-forming probe of the first pair of dimer-forming probes, and each dimer-forming probe of the second pair of dimer-forming probes, comprises a 5'-side region, a central region, and a 3'-side region,
the central regions of the dimer-forming probes of the first pair of dimer-forming probes are complementary to each other, and the central regions of the dimer-forming probes of the second pair of dimer-forming probes are complementary to each other,
the 3'-side regions of the dimer-forming probes of the first pair of dimer-forming probes are different from each other and not complementary to the opposing 5'-side regions of the dimer-forming probes of the first pair of dimer-forming probes,
the 3'-side regions of the dimer-forming probes of the second pair of dimer-forming probes are different from each other and not complementary to the opposing 5'-side regions of the dimer-forming probes of the second pair of dimer-forming probes,
the 5'-side regions of the dimer-forming probes of the first pair of dimer-forming probes are complementary to the 5'-side regions of the dimer-forming probes of the second pair of dimer-forming probes,
the 3'-side regions of the dimer-forming probes of the first pair of dimer-forming probes are complementary to the 3'-side regions of the dimer-forming probes of the second pair of dimer-forming probes,
the assist probe has a region complementary to a 5'-side region of a dimer-forming probe of the first pair of dimer-forming probes, a region complementary to an opposing 3'-side region of the dimer-forming probe of the first pair of dimer-forming probes, and a target region capable of binding to the target substance, and the target substance, assist probe and the plurality of pairs of dimer-forming probes are nucleic acids.

7. A kit for detection of a target substance, comprising a plurality of pairs of dimer-forming probes and an assist probe, wherein:

the plurality of pairs of dimer-forming probes comprise at least a first pair of dimer-forming probes and a second pair of dimer-forming probes, each dimer-forming probe of the first pair of dimer-forming probes, and each dimer-forming probe of the second pair of dimer-forming probes, comprises a 5'-side region, a central region, and a 3'-side region, the central regions of the dimer-forming probes of the first pair of dimer-forming probes are complementary to each other, and the central regions of the dimer-forming probes of the second pair of dimer-forming probes are complementary to each other, the 3'-side regions of the dimer-forming probes of the first pair of dimer-forming probes are different from each other and not complementary to the opposing 5'-side regions of the dimer-forming probes of the first pair of dimer-forming probes, the 3'-side regions of the dimer-forming probes of the second pair of dimer-forming probes are different from each other and not complementary to the opposing 5'-side regions of the dimer-forming probes of the second pair of dimer-forming probes, the 5'-side regions of the dimer-forming probes of the first pair of dimer-forming probes are complementary to the 5'-side regions of the dimer-forming probes of the second pair of dimer-forming probes, the 3'-side regions of the dimer-forming probes of the first pair of dimer-forming probes are complementary to the 3'-side regions of the dimer-forming probes of the second pair of dimer-forming probes, the assist probe has a region complementary to a 5'-side region of a dimer-forming probe of the first pair of dimer-forming probes, a region complementary to an opposing 3'-side region of the dimer-forming probe of the first pair of dimer-forming probes, and a target region capable of binding to a target substance, and the target substance, assist probe and the plurality of pairs of dimer-forming probes are nucleic acids.

\* \* \* \* \*